United States Patent [19]

DeCarlo, Jr. et al.

[11] Patent Number: 5,540,694
[45] Date of Patent: Jul. 30, 1996

[54] INSTRUMENT FOR CUTTING BONE

[75] Inventors: Alfred F. DeCarlo, Jr., Stamford, Conn.; Michael DeMarco, Sr., Port Chester, N.Y.; J. Larry Hineline, Fairfield, Conn.

[73] Assignee: Joint Medical Products Corporation, Stamford, Conn.

[21] Appl. No.: 307,408

[22] Filed: Sep. 16, 1994

Related U.S. Application Data

[63] Continuation of Ser. No. 69,712, Jun. 1, 1993, abandoned.

[51] Int. Cl.⁶ .......................... A61B 17/16; A61B 17/17
[52] U.S. Cl. ................................................. 606/80
[58] Field of Search .................... 606/79, 80, 86, 606/87, 89, 96; 408/226, 241 B, 704

[56] References Cited

U.S. PATENT DOCUMENTS

| | | | |
|---|---|---|---|
| 3,778,180 | 12/1973 | Ostrom | 408/226 |
| 4,080,093 | 3/1978 | Maier | 408/226 |
| 4,345,899 | 8/1982 | Vlock | 408/226 |
| 4,777,942 | 10/1988 | Frey et al. | |
| 4,790,852 | 12/1988 | Noiles | |
| 5,002,578 | 3/1991 | Luman | |
| 5,102,271 | 4/1992 | Hemmings | 408/226 |

FOREIGN PATENT DOCUMENTS

| 3538654 | 4/1987 | Germany | 606/80 |
|---|---|---|---|

OTHER PUBLICATIONS

Product brochure entitled "The Freeman Total Hip System," Corin Medical Limited, Gloucestershire, England, 1985.

Primary Examiner—Tamara L. Graysay
Attorney, Agent, or Firm—Maurice M. Klee

[57] ABSTRACT

A surgical instrument 20 for machining a precise cavity in a patient's bone for receiving a prosthesis 13 having a conical portion 6 and a triangular portion 8 is provided. The instrument 20 includes a first member 26 which has (i) a conical portion 44 which defines a longitudinal axis 40 and (ii) a guide path 46, 76 for receiving a movable second member 24. The movable second member 24 carries a triangle cutter 22. The movable second member 24 is moved along the longitudinal axis 40 to cut bone until an appropriate index 30 on the movable second member 24 is aligned with a reference surface 28 on the first member 26. This alignment indicates that the triangular cavity formed by cutter 22 is of the appropriate size for the triangular portion 8 of the prosthesis 13 which is to be implanted.

9 Claims, 3 Drawing Sheets

INSTRUMENT FOR CUTTING BONE

This application is a continuation of application Ser. No. 08/069,712, filed on Jun. 1, 1993, now abandoned.

BACKGROUND OF THE INVENTION

1. Field of the Invention

This invention relates to the field of artificial joint prostheses and, in particular, to an improved instrument for machining a precise cavity in bone for receiving a prosthesis.

2. Description of the Prior Art

Noiles, U.S. Pat. No. 4,790,852, (hereinafter the "'852 patent"), describes a hip joint prosthesis employing a sleeve having an external configuration designed to mate with the internal configuration of the hard bone at the location where the prosthesis is implanted. A similar overall prosthesis geometry is shown in U.S. Pat. No. 5,002,578.

FIGS. 1 and 2 hereof show the sleeve of the '852 patent. As shown therein, sleeve 13 has a conical portion 6 centered on the sleeve's longitudinal axis 36 and a triangularly-shaped projection 8 which is offset from and extends away from the longitudinal axis. As shown in FIG. 2, the triangularly-shaped projection can be varied to make a set of sleeves of various sizes to fit different geometries in the bone.

The combination of a cone and a triangle can be precisely cut in the patient's bone using, for example, the instrument and technique shown in FIGS. 4–7 of the '852 patent. FIG. 7 of the '852 patent is repeated as FIG. 3 hereof. As shown therein, instrument 66 includes shaft 62 for aligning the instrument with the center of the bone and cutter 64 for cutting the cavity for the prosthesis' triangular projection. The triangular cavity is formed by moving the entire instrument 66 into the bone in the direction shown by arrow 70.

Although the instrument of the '852 patent has worked successfully in practice, it has suffered from the limitation that it does not define a positional relationship between the cone portion and the triangular portion of the prosthesis cavity. That is, the size of the triangular part of the cavity formed by the instrument depends upon how far the instrument is advanced into the bone by the surgeon. In practice, this problem has been addressed by having the surgeon select a sleeve having a triangular projection which most closely matches the size of the cut cavity. That is, in terms of FIG. 2, the surgeon selects a sleeve having the "A", "C", or "E" projection depending upon the size of the cavity he or she has cut. See the '852 patent at column 6, line 62, to column 7, line 4.

In implanting a prosthetic joint, a surgeon may prefer to select prosthesis component sizes prior to surgery. For the reasons described above, this is difficult to do with the instrument of the '852 patent. Specifically, it is difficult for a surgeon to select the size of the prosthesis' projection in advance since that size will depend upon how far the '852 instrument is advanced into the bone. That is, because the size of the triangular cavity is completely dependent on the depth to which the instrument is moved into the bone and because there is no reference as to that depth, the surgeon cannot cut a triangular cavity of a pre-selected size.

Another instrument for preparing a similar type of cavity has been developed in which the cutter for the triangular projection is pivoted about its distal end. Reference is made to Corin product brochure entitled "The Freeman Total Hip System," Corin Medical Limited, Gloucestershire, England, 1985. This approach can allow the surgeon to select the size of the triangular projection in advance. However, this device suffers from the disadvantage that a separate instrument is needed for each different projection size. That is, in terms of FIG. 2, three instruments would be needed to cut cavities for the "A", "C", and "E" projections A pivoting instrument for cutting a cavity in the proximal end of the femur is shown in U.S. Pat. No. 4,777,942. This instrument cuts a cavity whose margin is an arc, rather than a straight line as needed to form a triangular-shaped cavity.

SUMMARY OF THE INVENTION

In view of the foregoing state of the art, it is an object of this invention to provide improved apparatus for cutting a cavity in bone for receiving a prosthesis having a conical portion and a projection of a generally triangular profile. More particularly, it is an object of the invention to provide cutting apparatus for cutting a triangular cavity having a predetermined geometric relationship with a pre-existing conical cavity. It is a further object of the invention to provide such apparatus wherein more than one such geometric relationship can be established by the apparatus.

To achieve the foregoing and other objects, the invention provides a surgical instrument for cutting a cavity in a patient's bone comprising:

(a) a first member comprising:
   (i) a conical portion which defines a longitudinal axis; and
   (ii) receiving means for receiving a movable second member;

(b) a movable second member which is received by the receiving means and is movable with respect to the first member along the longitudinal axis, said movable second member comprising means for carrying a cutter; and (c) a cutter for cutting a cavity having a generally triangular profile;

wherein the first and second members include means for indicating the longitudinal position of the second member relative to the first member.

In certain preferred embodiments of the invention, the second member includes means for withdrawing the first member from the patient's bone. In other preferred embodiments, the cutter comprises a cutting surface having an outer diameter and a bearing surface at one end of the cutting surface having an outer diameter larger than the outer diameter of the cutting surface. In further preferred embodiments, a set of cutters are provided all of which can be used with a common movable second member.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention.

BRIEF DESCRIPTION OF THE DRAWINGS

FIG. 7 is a perspective view of a cutter of a different size than the one in FIG. 4 for use with the instrument of the present invention.

DESCRIPTION OF THE PREFERRED EMBODIMENTS

Figure 4:
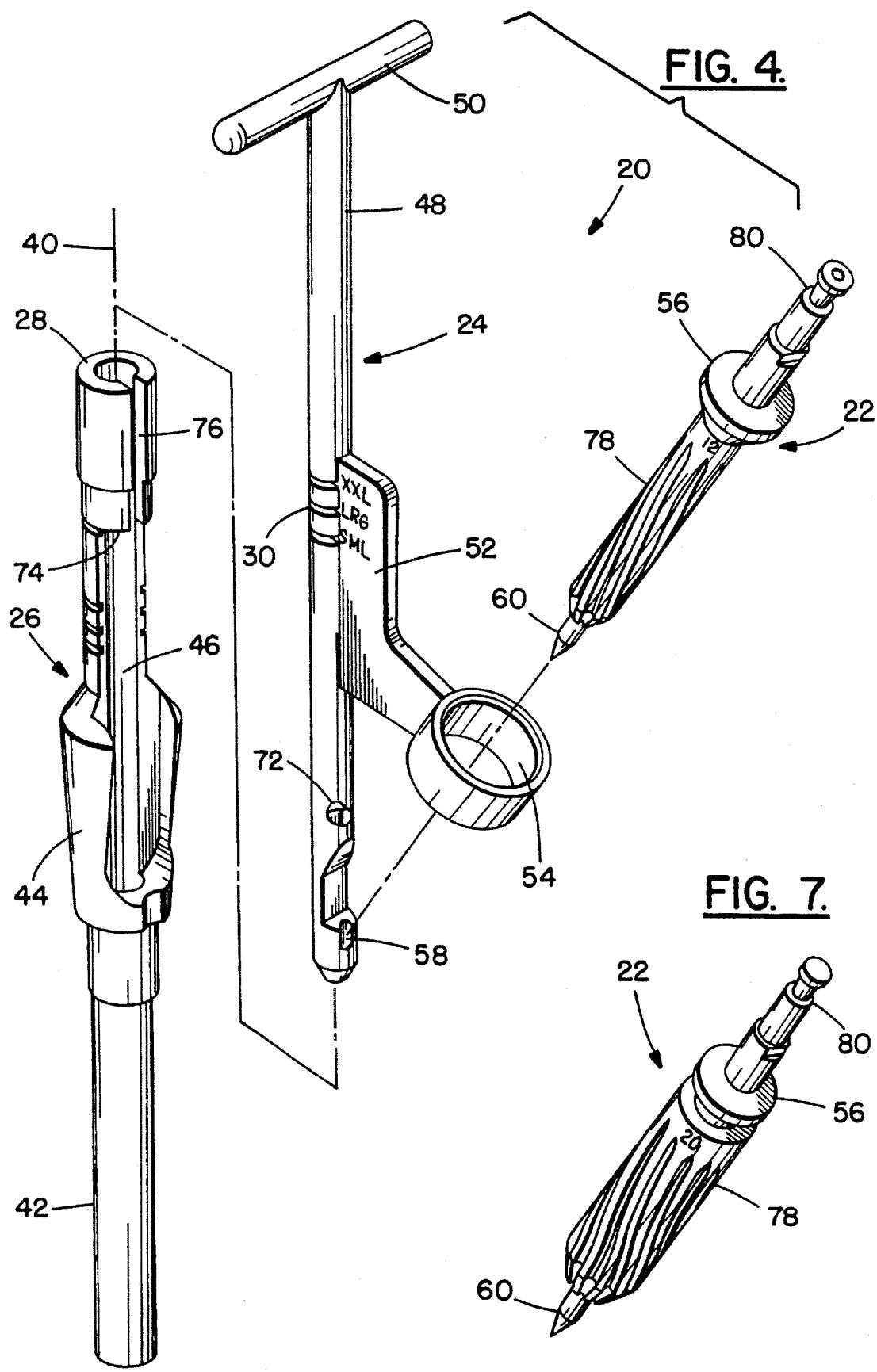
FIG. 4 is an exploded view of the surgical instrument of the present invention showing a cutter for use with the instrument.

With reference now to the drawings, wherein like reference characters designate like or corresponding parts throughout the several views, there is shown in FIG. 4 an exploded view of surgical instrument 20 constructed in accordance with the invention. Instrument 20 includes cutting means 22 for cutting the desired triangular-shaped cavity, carrying means 24 for carrying the cutting means, registering means 26 for registering the instrument with a pre-existing conical cavity in the patient's bone, and indicating means 28,30 for indicating the longitudinal location of carrying means 24 relative to registering means 26.

Registering means 26 has a longitudinal axis 40 which extends through pilot shaft 42 which is removably attached to the main body of the registering means by, for example, a screw thread. The registering means also has an external conical surface 44 which engages the wall of the pre-existing conical cavity. In addition, the registering means has receiving means 46 for receiving carrying means 24 and allowing the carrying means to move along longitudinal axis 40.

Carrying means 24 has a shaft 48 which at its upper end includes handle 50. Extending outward from shaft 48 is bracket 52 which carries bearing 54 which engages complementary cutter bearing 56 on cutting means 22. Bracket 52 comprises means for removably receiving cutting means 22. Shaft 48 also includes bearing hole 58 which engages complementary cutter bearing 60 on cutting means 22. Shaft 48 includes pin 72 which engages surface 74 of registering means 26 during withdrawal of the registering means from the patient's bone (see below).

Shaft 48 is sized to fit within receiving means 46 of registering means 26 with bracket 52 being slidable in slot 76 formed in the upper portion of the registering means. Pin 72 is also sized to fit through slot 76. Bracket 52 and pin 72 are located at different angular positions around the circumference of shaft 48 so that the shaft must be rotated about its longitudinal axis to first align pin 72 with slot 76 and then sequentially align bracket 52 with that slot during assembly of the instrument.

During assembly of instrument 20, cutting means 22 is inserted into carrying means 24 after carrying means 24 has been assembled into registering means 26. As shown in FIG. 4, a family of cutting means 22 are preferably provided to the surgeon with all members of the family having common sized bearing surfaces 56 and 60. In all cases, bearing surface 56 preferably has an outer diameter which is larger than the outer diameter of cutting surface 78. The cutting means also includes shaft 80 for connection to a drive means (not shown) for turning the cutter. The drive means can be hand or power operated and advances with the cutting means as that means is moved into the bone by the surgeon through the use of handle 50 of carrying means 24.

As discussed above, carrying means 24 and registering means 26 include indicating means 28,30. Indicating means 30 comprises three indices corresponding to three different triangles, referred to as small ("SML"), large ("LRG"), and double extra large ("XXL") in the figures. More or less indices can be used as desired and, of course, can be otherwise designated. Indicating means 28 comprises the upper end of registering means 26.

Figure 2:
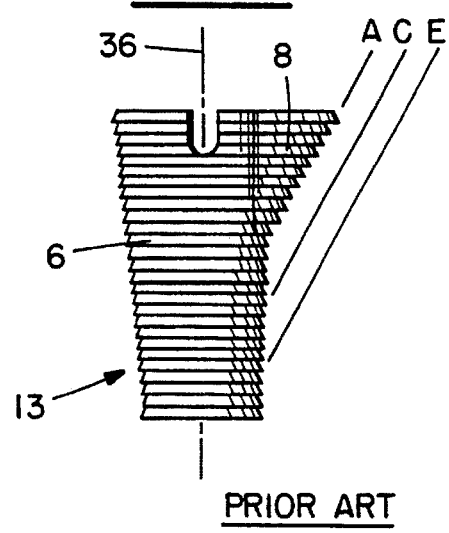
Figure 3:
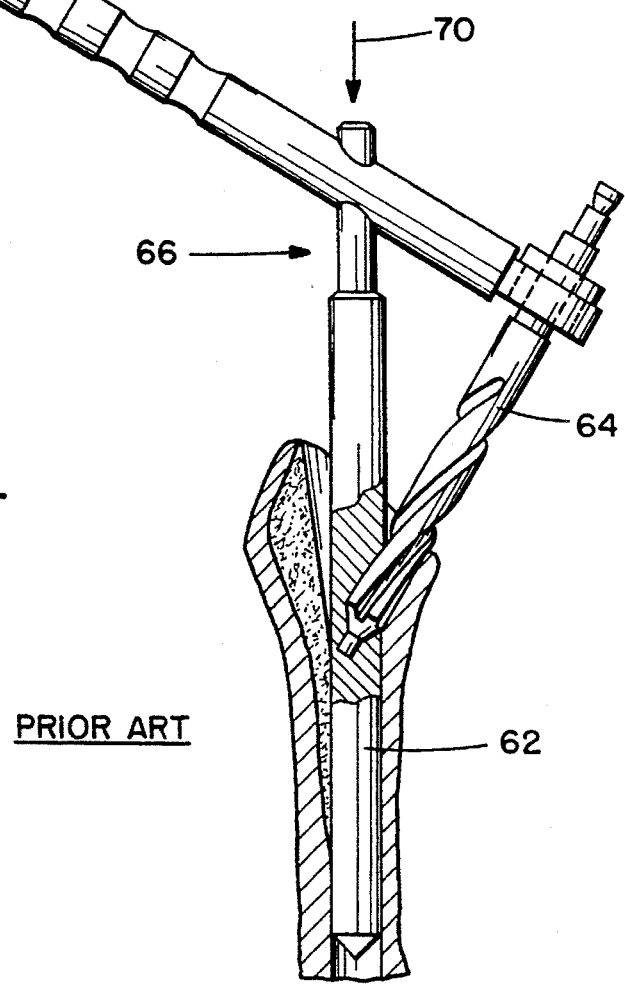
FIG. 3 shows the prior art surgical instrument of the U.S. Pat. No. 4,790,852.
Figure 5:
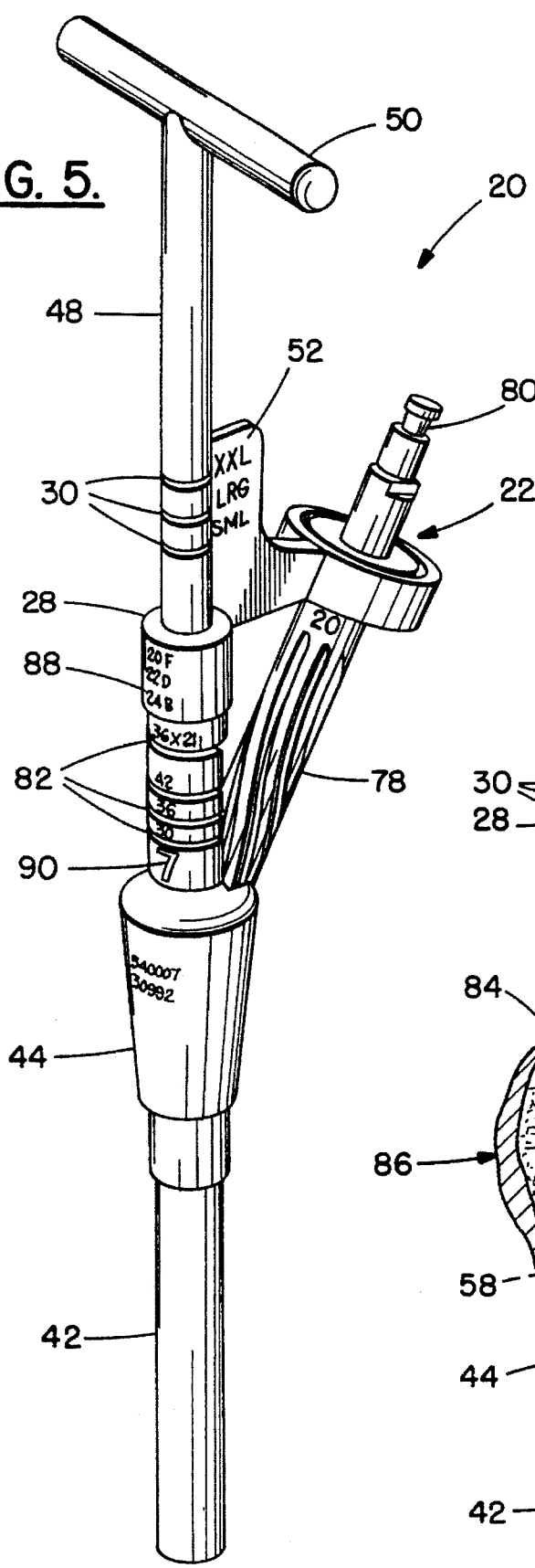
FIG. 5 is a perspective view of the surgical instrument of the present invention when assembled.
Figure 6:
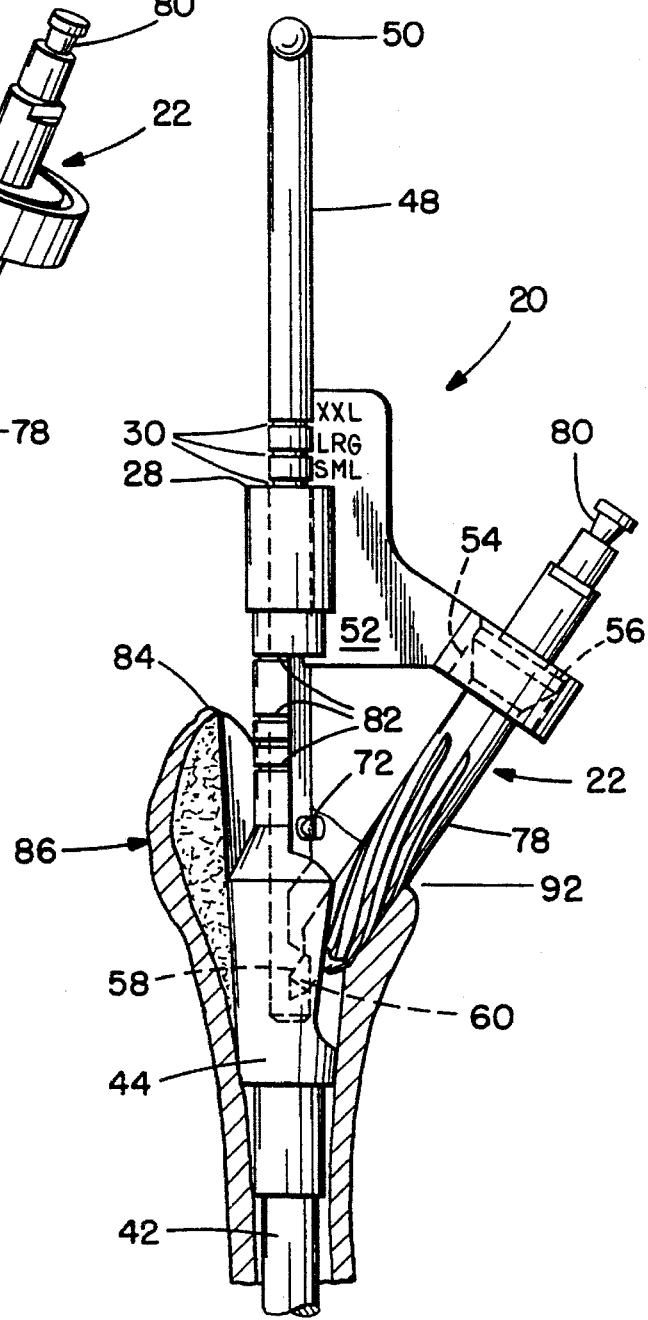
FIG. 6 is a front view, partially in section, illustrating the cutting of a patient's femur with the surgical instrument of the present invention.

The operation of the indicating means can be seen most clearly in FIGS. 5 and 6. FIG. 5 shows the configuration of the instrument with indicating means 30 substantially above indicating means 28. This corresponds to the configuration of the instrument prior to the cutting of the triangular-shaped cavity. FIG. 6 shows the configuration of the instrument with indicating means 28 in alignment with the "SML" index of indicating means 30. This corresponds to cutting means 22 having progressed into the bone sufficiently far to accept a prosthesis having a "small" triangular-shaped projection 8, e.g., projection "A" of FIG. 2. If this is the prosthesis which the surgeon wishes to use, the cutting process would be stopped at this point. However, if the surgeon wishes to use a prosthesis having a larger triangular-shaped projection, he or she would continue advancing the cutting means until either the "LRG" or "XXL" index 30 was aligned with reference surface 28.

Registering means 26 can include indicia 82 which relate to the geometry of the neck of the femoral prosthesis which is to be implanted. As shown in FIG. 6, these indicia are referenced to the most proximal portion 84 of the great trochanter 86 of the patient's femur. The index which lines up with proximal portion 84 provides the surgeon with information regarding selecting the appropriate neck geometry for the femoral component. Additional notations can be included on registering means 26 to indicate the sleeve cone sizes for which the registering means is appropriate (see reference numeral 88 in FIG. 5). A general reference number to the cone size can also be imprinted on the registering means (see reference numeral 90 in FIG. 5).

The overall procedure in which instrument 20 is used is as follows. First, the patient's femur is prepared by cutting with a straight reamer to establish an extended cavity and center line for receipt of the distal stem of the femoral prosthesis. Second, the proximal femur is reamed with a conical reamer to form a cavity for receiving the conical portion 6 of sleeve 13. This conical cavity is on the same center line as the straight cavity and the reaming is conducted until the proximal end of the reamer is even with the proximal end of the resected femur (see reference numeral 92 in FIG. 6).

Third, surgical instrument 20 in its assembled form as shown in FIG. 5 is inserted into the proximal end of the femur. The assembled instrument includes a cutting means 22, a registering means 26, and a pilot shaft 42 which are appropriate to 1) the size of the triangular projection of the sleeve which the surgeon wishes to implant, and 2) the straight and conical cavities formed in the bone in steps 1 and 2.

Figure 1:
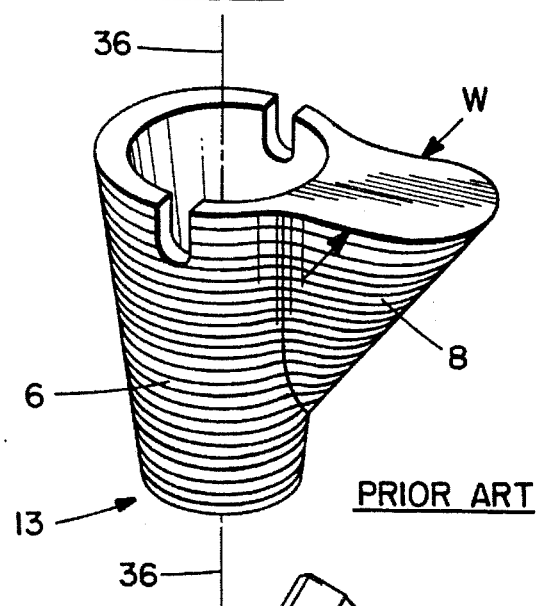
FIGS. 1 and 2 show the prior art prosthetic sleeve of the U.S. Pat. No. 4,790,852.

Specifically, the diameter of cutting means 22 is selected based on the width W of the triangular projection of the sleeve which is to be implanted (see FIG. 1). The registering means 26 is selected based on the size of the conical reamer used in step 2. Specifically, conical portion 44 of registering means 26 has the same taper and same maximum diameter as the conical reamer. The height of conical portion 44 is preferably slightly less than the height of the conical reamer so that the proximal end of the conical portion can be aligned with the resected end 92 of the femur without bottoming out in the reamed conical cavity. The pilot shaft 42 is selected based on the size of the straight reamer used in step 1 which in turn is selected by the surgeon based on the inside diameter of the patient's femur.

To provide the surgeon with the ability to match the finished prosthesis to various patient requirements, sleeves 13 of various sizes and configurations and femoral prostheses having various proximal and distal diameters are provided to the surgeon along with corresponding sets of cutting means 22, pilot shafts 42, registering means 26, and straight and conical reamers. Preferably, only a single carrying means 24 is used in the overall system, such carrying means being able to accept all cutting means 22 and being receivable in all registering means 26.

The initial insertion of instrument 20 into the cavity in the femur brings the proximal end of conical portion 44 into alignment with the proximal end 92 of the resected femur. At this point, the surgeon can use indicia 82 to confirm his or her selection of a neck geometry for the femoral prosthesis.

Cutting means 22 is then rotated by the driving means (not shown) while carrying means 24 is moved along longitudinal axis 40 of registering means 26. This process is continued until the appropriate index 30 on carrying means 24 is aligned with reference surface 28, e.g., until the "LRG" index is aligned if the sleeve to be inserted is to have a "LRG" triangular projection. In some cases, the original choice of triangular projection may be too small to reach the patient's hard bone at the proximal end of the femur, in which case the cutting of the triangular cavity would be continued to the next index mark and a further evaluation would be made at that point. If suitable at this point, a sleeve having a triangular portion corresponding to the index mark to which the cutting was continued would be used. Depending upon the circumstances, all or portions of the process may be repeated until a suitable fit is achieved.

Instrument 20 is removed from the patient's femur by pulling carrying means 24 straight out using handle 50 while rotating the handle to ensure the engagement of pin 72 with surface 74 of registering means 26. A light tap on the handle from below is usually sufficient to release registering means 26 from the patient's bone allowing complete removal of the instrument. Implantation of the femoral prosthesis then follows.

Instrument 20 is fabricated using conventional techniques used in the manufacture of surgical instruments. Similarly, the instrument is composed of conventional stainless steels or other materials employed in constructing surgical instruments.

Although preferred and other embodiments of the invention have been described herein, other embodiments may be perceived by those skilled in the art without departing from the scope of the invention as defined by the following claims. For example, although the invention has been described in terms of the implantation of the femoral portion of a hip prosthesis, it can be used with prostheses for other joints such as the shoulder, knee, or elbow.

What is claimed is:

1. Apparatus for creating a cavity in a bone, said cavity (i) having a cross section which has a generally triangular profile and (ii) being contiguous with a pre-existing conical cavity in the bone, said apparatus comprising:
   (a) cutting means for cutting said cavity;
   (b) carrying means for carrying the cutting means;
   (c) registering means for registering the apparatus with the pre-existing conical cavity, said registering means having:
      (1) a longitudinal axis;
      (2) an external surface a portion of which engages the wall of the pre-existing conical cavity; and
      (3) receiving means for receiving the carrying means and allowing the carrying means to move along the longitudinal axis; and
   (d) indicating means for indicating the longitudinal location of the carrying means relative to the registering means.

2. The apparatus of claim 1 wherein the carrying means includes means for withdrawing the registering means from the bone.

3. The apparatus of claim 1 wherein the carrying means comprises means for removably receiving the cutting means.

4. The apparatus of claim 3 wherein the cutting means comprises a cutting surface having an outer diameter and a bearing surface at one end of the cutting surface having an outer diameter larger than the outer diameter of the cutting surface and wherein the means for removably receiving the cutting means comprises a bearing surface for mating with said bearing surface of the cutting means.

5. Apparatus for creating a cavity in a bone for receiving a prosthesis which has a conical portion and a projection of a generally triangular profile, said apparatus comprising:
   (a) a first member comprising:
      (i) a conical portion which defines a longitudinal axis; and
      (ii) receiving means for receiving a movable second member;
   (b) a movable second member which is received by the receiving means and is movable with respect to the first member along the longitudinal axis, said movable second member comprising carrying means for carrying a cutter; and
   (c) a cutter for cutting a cavity having a generally triangular profile, said cutter being carried by said carrying means;
   wherein the first and second members include means for indicating the position of the second member relative to the first member.

6. The apparatus of claim 5 wherein the second member includes means for withdrawing the first member from bone.

7. The apparatus of claim 5 wherein the cutter and the carrying means include mating bearing surfaces.

8. The apparatus of claim 5 wherein the cutter comprises a cutting surface having an outer diameter and a bearing surface at one end of the cutting surface having an outer diameter larger than the outer diameter of the cutting surface and wherein the carrying means comprises a bearing surface for mating with said bearing surface of the cutter.

9. A method for cutting a triangular cavity in bone comprising:
   providing a cutter which comprises a cutting surface having an outer diameter and a cutter bearing at one end of the cutting surface having an outer diameter larger than the outer diameter of the cutting surface;
   providing a cutter carrying means which comprises a cutter carrying means bearing which is complementary to the cutter bearing and which has an inner diameter which is larger than the outer diameter of the cutter's cutting surface;
   journaling the cutter bearing in the cutter carrying means by passing the cutter's cutting surface through the cutter carrying means bearing and engaging the cutter bearing with the cutter carrying means bearing; and
   cutting the cavity by moving the cutter carrying means relative to the bone.

* * * * *